(12) United States Patent
Ortiz et al.

(10) Patent No.: US 7,754,487 B2
(45) Date of Patent: Jul. 13, 2010

(54) HEMATOLOGY LINEARITY CONTROL COMPOSITION, SYSTEM AND METHOD OF USE

(75) Inventors: Nery Ortiz, Miami, FL (US); Theodore J. Gerula, Fort Lauderdale, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 286 days.

(21) Appl. No.: 11/938,853

(22) Filed: Nov. 13, 2007

(65) Prior Publication Data

US 2008/0113438 A1 May 15, 2008

Related U.S. Application Data

(60) Provisional application No. 60/865,661, filed on Nov. 14, 2006.

(51) Int. Cl.
*G01N 33/48* (2006.01)

(52) U.S. Cl. .............................. 436/10; 436/8; 436/63; 436/66; 435/2; 252/408.1

(58) Field of Classification Search ...................... 436/8, 436/10, 63, 71, 66; 435/2, 29; 422/73; 252/408.1
See application file for complete search history.

(56) References Cited

U.S. PATENT DOCUMENTS

| | | | |
|---|---|---|---|
| 3,873,467 A * | 3/1975 | Hunt ............................ 436/10 |
| 4,264,470 A | 4/1981 | Chastain et al. |
| 4,299,726 A | 11/1981 | Crews et al. |
| 4,358,394 A | 11/1982 | Crews et al. |
| 4,389,490 A | 6/1983 | Crews et al. |
| 4,405,719 A | 9/1983 | Crews et al. |
| 4,704,364 A | 11/1987 | Carver et al. |
| 5,125,737 A | 6/1992 | Rodriguez et al. |
| 5,320,964 A | 6/1994 | Young et al. |
| 5,492,833 A | 2/1996 | Rodriguez et al. |
| 5,512,485 A | 4/1996 | Young et al. |
| 5,616,501 A | 4/1997 | Rodriguez et al. |
| 5,648,225 A | 7/1997 | Kim et al. |
| 5,858,790 A | 1/1999 | Kim et al. |
| 5,874,310 A | 2/1999 | Li et al. |
| 5,879,900 A | 3/1999 | Kim et al. |
| 5,917,584 A | 6/1999 | Li et al. |
| 6,060,322 A | 5/2000 | Horton et al. |
| 6,187,590 B1 | 2/2001 | Kim et al. |
| 6,200,500 B1 | 3/2001 | Ryan |
| 6,221,668 B1 | 4/2001 | Ryan et al. |
| 6,399,388 B1 | 6/2002 | Ryan et al. |
| 6,403,377 B1 | 6/2002 | Ryan et al. |
| 6,406,915 B2 | 6/2002 | Ryan et al. |
| 6,410,330 B1 | 6/2002 | Li et al. |
| 6,448,085 B1 | 9/2002 | Wang et al. |
| 6,472,215 B1 | 10/2002 | Huo et al. |
| 6,653,137 B2 | 11/2003 | Ryan |
| 6,673,618 B1 | 1/2004 | Li et al. |
| 6,723,563 B2 | 4/2004 | Ryan |
| 6,744,245 B2 | 6/2004 | Taylor et al. |
| 7,008,792 B2 | 3/2006 | Lopez et al. |
| 7,208,319 B2 | 4/2007 | Lopez et al. |
| 2003/0104631 A1 | 6/2003 | Carver et al. |
| 2005/0079623 A1 | 4/2005 | Ortiz et al. |

* cited by examiner

*Primary Examiner*—Maureen M Wallenhorst
(74) *Attorney, Agent, or Firm*—Cuspa Technology Law Associates; Mitchell E. Alter (57) ABSTRACT

A linearity control system includes a series of linearity control compositions, each thereof includes white blood cell analogs and stabilized red blood cells in a suspension medium. The concentration of the white blood cell analogs in the series of control compositions increases from $0.2 \times 10^3$ to $800 \times 10^3$ analogs per microliter, and the concentration of the white blood cell analogs in at least one control composition is greater than $120 \times 10^3$ analogs per microliter. The stabilized red blood cells facilitate mono-dispersion of the white blood cell analogs in the suspension medium by gently mixing. The control compositions further include platelet analogs, or additionally include reticulocyte and/or nucleated red blood cell analogs. The linearity control system allows the verification of the reportable measurement range and linearity of the measurements of hematology analyzers for white blood cells, red blood cells and platelets in extended concentration ranges.

26 Claims, 2 Drawing Sheets

Fig. 4

HEMATOLOGY LINEARITY CONTROL COMPOSITION, SYSTEM AND METHOD OF USE

CROSS REFERENCE TO RELATED APPLICATION

This application claims the benefit under 35 USC 119(e) of the provisional patent application Ser. No. 60/865,661, filed on Nov. 14, 2006, which is hereby incorporated by reference in its entirety.

FIELD OF THE INVENTION

The present invention relates to a linearity reference control composition and a linearity control system that enables verification of the reportable measurement range and linearity of the measurements of hematology analyzers for white blood cells, red blood cells and platelets in extended concentration ranges.

BACKGROUND OF THE INVENTION

Quality control has long been a necessary and routine procedure in clinical hematology. Accuracy in the counting of various types of blood cells is dependent, in part, upon the use of adequate control products and methods of using the control products. With the numerous types of equipment for particle counting now available, quality control by the use of control products is necessary, since the possibility of an instrument malfunctioning is ever present. The traditional method of maintaining a quality control program for automatic particle counting equipment has consisted of providing fresh human blood as a whole blood standard. However, this fresh blood is usable for only one day, therefore, various manufactured control products which have longer product lifetime have been developed.

Commonly used particles in a control product simulate or approximate the types of particles or cells that are intended to undergo analysis. Consequently, these particles are often referred to as analog particles. The analog particles are selected or designed so that they have certain characteristics that are similar to those of the particles or cells to be analyzed in the instruments. Exemplary characteristics include similarities in size, volume, surface characteristics, granularity properties, light scattering properties and fluorescence properties.

Various commercial reference control products are now available, which use various processed or fixed human or animal blood cells as analogs of human blood cells. U.S. Pat. No. 5,512,485 (to Young et al) teaches a hematology control comprising several white blood cell analogs made of processed and fixed animal nucleated blood cells. These white blood cell analogs are designed to have characteristics similar to subpopulations of white blood cells. Commercially available hematology controls can also contain red blood cell, platelet, reticulocyte and nucleated red blood cell components, and many of them are made of cellular analogs. Furthermore, certain non-nucleated red blood cells, such as human, turkey, and shark red blood cells, have been used for making analogs of white blood cell subpopulations for hematology reference controls, such as those described in U.S. Pat. No. 4,704,364 (to Carver et al).

The control products have been used to determine whether an instrument is properly functioning according to manufacturer's specifications. These control products can be divided into two types. The first type is an integrated control which contains more than one type of cellular components, for example, red blood cell, white blood cell and platelet components. Commercial examples of the first type of control products include Beckman Coulter, Inc.'s COULTER® 4C® Cell Controls and Streck Laboratories, Inc.'s Para 12® Cell Controls. These products are typically configured in three levels, i.e., normal, abnormal high and abnormal low, which simulate commonly seen normal and clinically abnormal blood samples. However, these integrated controls can not be used to test and verify the entire reportable ranges for various measurements of the hematology analyzers, because the concentrations of individual components are not sufficiently high or low. It is known that increasing concentration of components creates problems because of aggregation of cellular particles in the integrated control product.

Consequently, the second type of control products have been developed, which are specifically designed for testing the reportable range of various measurements on hematology analyzers and determine linearity of the reported parameters. The second type of control products typically contain a single blood cell component, such as white blood cell analog only or platelet analog only, at various concentrations over reportable range of a particular instrument. In this manner the problems associated with integrated controls that contain more than one type of blood cell components is avoided to a certain degree. Examples of the second type of control products include Streck Laboratories CVA products and R&D Systems CBC-Line Linearity Kits.

However, the existing control products of the second type have various deficiencies. First, using the single component linearity controls for determining linearity of measurements of several hematology parameters are time consuming and labor intensive. Currently, red blood cell count, white blood cell count, platelet count, and hemoglobin concentration are the reportable parameters most frequently subjected to confirmation of linearity of their measurements. Typically, five to eight control compositions with various concentrations are required for testing the entire reportable range for each reportable parameter. Consequently, the existing linearity control kit contains a substantial number of control vials, for example, more than 20 control vials for linearity determinations of the four parameters mentioned above. Commonly, it takes more than one hour for testing all control vials of a linearity control kit.

Secondly, at high concentrations the individual blood cell components still tend to aggregate or clump together causing difficulty in using the product. The aggregation has been found to occur especially at high concentration of white blood cell analogs. Before using these control products, vigorous agitation has been required to disperse the cellular particles. This is time consuming, which typically takes several minutes for mixing and settling the WBC controls prior to being used on the instrument to be tested. Moreover, vigorous agitation can be deleterious to the cellular components in the control composition, as such the existing linearity control kits commonly require different mixing procedures for different cell components. For example, in R&D Systems CBC-Line Linearity Kits each tube of the WBC & PLT controls is required to be mixed by vortexing for 2 minutes, then settling for 10 minutes to allow dissipation of microbubbles, and rapidly inverting 8 to 10 times immediately before use on the instrument; while the RBC controls are required to be mixed by manual rotations of the tubes between palms, without vortex or mechanical mixing.

Still further, some of the second type of control products are provided as a single component concentrate which requires manual dilution by the operator. This not only requires further time in preparing the control compositions prior to the test of the instrument, and it also introduces additional errors to the measurements. In this case, the reference values are established by the operator based on the dilution, which are not regulated by the manufacturer of the control products.

Consequently, there is a strong need for improved linearity control compositions and an improved linearity control system that solves one or more of these problems.

SUMMARY OF THE INVENTION

In one aspect, the present invention is directed to a linearity control composition, which comprises white blood cell analogs in a concentration greater than $120 \times 10^3$ analogs, preferably $150 \times 10^3$ analogs per microliter, a predetermined concentration of stabilized red blood cells, and a suspension medium; wherein the stabilized red blood cells facilitate mono-dispersion of the white blood cell analogs in the suspension medium by gently mixing. Preferably, the concentration of the stabilized red blood cells in the linearity control composition is at least $1.5 \times 10^6$ cells per microliter. The linearity control composition can comprise platelet analogs, optionally further comprise nucleated red blood cell analogs, reticulocyte analogs, or a combination thereof.

In a further aspect, the present invention is directed to a linearity control system, which comprises a series of linearity control compositions, each of the linearity control compositions comprising a predetermined concentration of white blood cell analogs, stabilized red blood cells in a concentration in a range from $0.1 \times 10^6$ to $9 \times 10^6$ cells per microliter, and a suspension medium; wherein the concentration of the white blood cell analogs in the series of control compositions increases in a range from $0.2 \times 10^3$ to $800 \times 10^3$ analogs per microliter, and in at least one, preferably in at least two, of the control compositions the concentration of the white blood cell analogs is greater than $120 \times 10^3$ analogs per microliter and the concentration of the stabilized red blood cells is at least $1.5 \times 10^6$ cells per microliter, and wherein the stabilized red blood cells facilitate mono-dispersion of the white blood cell analogs in the suspension medium by gently mixing. In the linearity control system, each of the control compositions is contained in a pre-packaged vial that does not require a manual dilution. The linearity control system further comprises a medium vial containing the suspension medium without cellular particles for establishing background of a measurement of which the linearity is to be assessed. Optionally, the linearity control system can further include one or more single component vials containing a single component selected from the group consisting of platelet analogs, stabilized red blood cells, reticulocyte analogs and nucleated red blood cell analogs.

In another aspect, the present invention is directed to a method of determining linearity of white blood cell enumeration of a hematology analyzer in an extended white blood cell concentration range. The method comprises the steps of: (a) providing a series of linearity control compositions; each of the control compositions comprising a predetermined concentration of white blood cell analogs, a predetermined concentration of stabilized red blood cells and a suspension medium; the concentration of the white blood cell analogs in the series of control compositions increasing in a range from $0.2 \times 10^3$ to $800 \times 10^3$ analogs per microliter and in at least one, preferably in at least two, of the control compositions greater than $120 \times 10^3$ analogs per microliter; (b) gently mixing the control compositions to disperse the white blood cell analogs and the stabilized red blood cells in the suspension medium; (c) analyzing each of the control compositions on a hematology analyzer, and obtaining a report value of the white blood cell count for each of the control compositions; and (d) determining linearity of the white blood cell enumeration in an extended range of the hematology analyzer using the report value and assay parameters of the control compositions.

In yet a further aspect, the present invention is directed to a method of determining linearity of enumerations of red blood cells, white blood cells, and platelets of a hematology analyzer in extended cell concentration ranges. The method comprises the steps of: (a) providing a series of control compositions; each of the control compositions comprising a predetermined concentration of white blood cell analogs, stabilized red blood cells in a concentration ranging from about $0.1 \times 10^6$ to about $9 \times 10^6$ cells per microliter, platelet analogs in a concentration up to $7,000 \times 10^3$ analogs per microliter, and a suspension medium; the concentration of the white blood cell analogs in the series of control compositions increasing in a range from $0.2 \times 10^3$ to $800 \times 10^3$ analogs per microliter and in at least one, preferably at least two, of the control compositions greater than $120 \times 10^3$ analogs per microliter; at least five of the control compositions having assay parameters of white blood cell count, and at least five of the control compositions having assay parameters of red blood cell count and hemoglobin concentration, and at least five of the control compositions having assay parameters of platelet count; (b) gently mixing the control compositions to disperse the analogs and the cells in the suspension medium; (c) analyzing each of the control compositions on a hematology analyzer, and obtaining report values of the white blood cell count, the red blood cell count, and the platelet count of each of the control compositions; and (d) determining linearity of enumerations of white blood cells, red blood cells, and platelets of the hematology analyzer using the report values and the assay parameters of the control compositions.

The gently mixing of the control compositions to disperse the analogs in the suspension medium comprises a mixing time of less than 90 seconds, preferably less than 50 seconds. All control compositions are used directly on the hematology analyzer after gently mixing, without a manual dilution. The method uses less than 14, preferably less than 12, control compositions, for determining linearity of enumerations of red blood cells, white blood cells, and platelets.

The advantages of the present invention will become apparent from the following description taken in conjunction with the accompanying drawings showing exemplary embodiments of the invention.

DETAILED DESCRIPTION OF THE INVENTION

In one aspect, the present invention provides a linearity reference control composition that comprises white blood cell analogs and stabilized red blood cells in a suspension media, wherein the stabilized red blood cells facilitate mono-dispersion of the white blood cell analogs in the suspension medium by gently mixing. Preferably, the linearity control composition further comprises platelet analogs. Optionally, the linearity control composition can further comprise reticulocyte analogs, nucleated red blood cell analogs, or a combination thereof.

In one embodiment, the linearity reference control composition comprises white blood cell analogs at a concentration greater than $120 \times 10^3$ analogs per microliter (µl), and preferably greater than $150 \times 10^3$ analogs per microliter. The concentration of the white blood cell analogs is selected according to the measurement range of a hematology analyzer. On hematology analyzers, white blood cell concentration (WBC) of a blood sample is reported in a unit of $\times 10^3$ per microliter, which is also commonly referred to as white blood cell count. For assessing the linearity of enumeration of white blood cells at a concentration beyond $100 \times 10^3/\mu l$, the linearity control composition can contain white blood cell analogs from $120 \times 10^3$ to less than $800 \times 10^3$ analogs per microliter.

The process of making the white blood cell analogs used in the linearity control composition has been described in detail in U.S. Pat. No. 4,704,364 (to Carver et al) and U.S. Pat. No. 5,512,485 (to Young et al), which are incorporated by references in their entirety. More particularly, the monocyte analog taught by Carver et al and the lymphocyte analog taught by Young et al are especially suited for the present invention. The process of making suitable white blood cell analogs is further provided in the examples described hereinafter.

In a further embodiment, the linearity reference control composition comprises two or more different types of white blood analogs, each representing a separate subpopulation of white blood cells, providing a total white blood cell analog concentration greater than $120 \times 10^3$ analogs per microliter, and preferably greater than $150 \times 10^3$ analogs per microliter. More specifically, the white blood cell analogs can include analogs of more than one subpopulation of white blood cells, for example, two, three, four or five white blood cell subpopulation analogs to simulate white blood cell subpopulations for a differential analysis.

Suitable examples of white blood cell analogs include stabilized and fixed mammalian white blood cells, and processed and/or fixed human and animal red blood cells, as known in the art. In one embodiment, the white blood cell analogs can be made from processed avian and human red blood cells for counting and differential analysis using an impedance measurement, as taught in U.S. Pat. No. 4,704,364, which is herein incorporated by reference in its entirety. In another embodiment, the white blood cell analogs can be made from processed goose or alligator red blood cells for differential analysis using a combination of impedance and light scatter measurement, as taught in U.S. Pat. Nos. 5,320,964 and 5,512,485, which are herein incorporated by reference in their entirety. In a further embodiment, the white blood cell analogs can be made from fixed mammalian white blood cells. The mammalian white blood cells are fixed prior to lysing the red blood cells in the whole blood during the preparation of the white blood cell analogs.

Optionally, the mammalian white blood cells and red blood cells can be further treated by contacting with a lipoprotein during the process of preparing the white blood cell analogs. The contact with lipoprotein can occur prior to fixing the white or red blood cells; and it can also occur after fixing and during storage in a suspension medium, as taught in U.S. Pat. Nos. 5,320,964, 5,512,485, 6,406,915, 6,403,377, 6,399,388, 6,221,668, and 6,200,500, which are herein incorporated by reference in their entirety.

As stated above, the linearity control composition comprises stabilized red blood cells. The concentration of the stabilized red blood cells in the linearity control composition ranges from approximately $0.1 \times 10^6$ to $9 \times 10^6$ cells per microliter. The stabilized red blood cells can be stabilized human or animal red blood cells, preferably, stabilized human red blood cells. The process of making the stabilized red blood cells has been described in detail in U.S. Pat. Nos. 4,299,726 and 4,358,394, which are herein incorporated by references in their entirety. A process of making suitable stabilized red blood cells is further provided in the examples described hereinafter.

The stabilized red blood cells in the linearity control composition serve several purposes. First, the stabilized red blood cells facilitate or aid in the dispersion of the white blood cells analogs. As described previously, the existing commercial linearity controls having a concentration of white blood cell analogs above $100 \times 10^3$ analogs per microliter often have extensive aggregation of the analogs, which requires vigorous mixing, and additional rapid inversions before the product is used on the hematology analyzers. These mixing steps can be time consuming, as well as, possibly being deleterious to one or more components in the linearity control composition, which may lead to erroneous results.

It is found unexpectedly by the present inventors that in the presence of a substantial amount of stabilized red blood cells, the white blood cell analogs in the linearity control composition at a substantially high concentration, such as at several hundred thousand, do not form extensive aggregations; the white blood cell analogs and the stabilized red blood cells can be mono-dispersed by gently mixing the instant linearity control composition packaged in control vials, in the same manner of mixing those reference controls that contain cellular particles at a concentration equivalent to a normal blood sample.

Although the mechanism of such an effect is not fully understood, it is believed that such effect is at least in part due to the fact that in the presence of a large amount of stabilized red blood cells, typically several times higher than the white blood cell analogs, the stabilized red blood cells effectively prevent the white blood cell analogs stacking or sticking together when these cellular particles settle down in the control composition during storage.

The term "gently mix" used herein includes manually rotating and/or inverting the container containing the control composition, such as a test tube or a vial, or slowly rotating the container mechanically, such as on a roller. The slow mechanical rotation is often used in the clinical laboratories for mixing human periphery blood samples collected in Vacutainer® tubes, typically at a speed from about 4 rpm to about 10 rpm. The speed of rotation for mixing the linearity control compositions of the present invention is equivalent to the speed of mixing human periphery blood samples.

Furthermore, the term "gently mix" used herein does not include mechanically stirring or vortex mixing. The mixing time of the linearity control compositions of the present invention is less than 90 seconds. Typically, the mixing time is less than 50 seconds, and preferably less than 40 seconds. Commonly, following the manual mixing procedure described in Example 7 the mixing time for individual control vials is about 20 to 30 seconds. The mixing time is defined as the time required to gently mix a control composition contained in a container such as a control vial to achieve a mono-dispersion of the analogs and/or cells in the composition prior to use on the hematology analyzer.

The term "mono-dispersion" used herein means that the particles are individually dispersed without aggregation between one and another. It is known that vigorous agitation tends to be deleterious to one or more components contained in the linearity control composition and can adversely affect the measurement of the component on the hematology analyzer. The linearity control compositions of the present invention can be mono-dispersed in the suspension medium by gently mixing the control vials in a short period of time as described above, which completely avoids vortex or other vigorous mixing modes. This is a major advantage of the present invention in comparison to the existing linearity control products in the art.

Secondly, incorporation of stabilized red blood cells into the linearity control composition enables one to have an integrated reference control composition comprising white blood cells analogs and stabilized red blood cells, so that separate sets for each component are unnecessary for verifying the reportable range of the hematology analyzer for both white blood cell and red blood cell enumerations. As can be understood, incorporation of stabilized red blood cells into the linearity control composition further enables verification of the reportable concentration range of hemoglobin and linearity of the hemoglobin measurement. On hematology analyzers, red blood cell concentration (RBC) of a blood sample is typically reported in the unit of $\times 10^6$ per microliter, which is also commonly referred to as red blood cell count; and hemoglobin concentration (Hgb) is reported in a unit of gram per deciliter (g/dl).

Moreover, in the measurement of white blood cells on hematology analyzers the red blood cells in a blood sample are lysed by a lytic reagent, and remaining white blood cells are counted or differentiated by the instruments. As can be appreciated, the presence of stabilized red blood cells in the instant linearity control composition, at equivalent concentrations to those in the human blood samples, further enables assessment of the reaction conditions including the quality of the lytic reagent, reaction time, temperature, and mixing, etc., on the hematology analyzer. This provides additional information which can not be obtained using a control composition that does not contain red blood cells.

Typically, the concentration of stabilized red blood cells increases with an increase in the concentration of white blood cell analogs, although at very high particle concentrations of individual components in the linearity control composition, the stabilized red blood cells concentration in the linearity control composition is proportionally reduced to avoid extensively high total particle concentration. For example, as stated previously the linearity control composition can optionally include platelet analogs. When the white blood cell analogs are increased, typically greater than $120 \times 10^3$ analogs per microliter, and the platelet analogs are increased, typically greater than $1 \times 10^6$ analogs per microliter, the concentration of the stabilized red blood cells can be reduced proportionally to avoid an excessively high total particle concentration. However, the concentration of stabilized red blood cells is at least $1.5 \times 10^6$, preferably greater than $2 \times 10^6$ cells per microliter to aid in dispersion of the white blood cell analogs, when the white blood cell analog concentration is greater than $120 \times 10^3$ analogs per microliter.

Optionally, the linearity control composition further includes platelet analogs. The platelet analog concentration in the linearity control composition can be from 0 up to $7 \times 10^6$ platelets per microliter. The platelet analogs can be stabilized human or animal platelets, or can be made from other cell types. One suitable example is using processed goat red blood cells as the platelet analog, as disclosed in U.S. Pat. Nos. 4,264,470, 4,389,490, and 4,405,719, which are incorporated by reference in their entirety.

In a preferred embodiment, the platelet analog concentration increases as the white blood cells analogs concentration increases. However, it is contemplated that the platelet analog concentration could decrease as the white blood cell analog and the stabilized red blood cell concentrations increase so that an excessively high total particle count is avoided in the linearity control composition.

In another embodiment of the present invention, the linearity control composition further comprises a reticulocyte analog for the analysis of reticulocytes. The reticulocyte analog can be made using the methods known in the art, for example, the methods described in U.S. Pat. Nos. 6,399,388, 6,403,377, and 6,406,915, which are herein incorporated by reference in their entirety. Like the platelet analog concentration, the reticulocyte analog concentration preferably increases with the increase concentration of the white blood cell analogs, but could also decrease with the increase of other components in the linearity control composition so that an excessively high total particle count is avoided in the linearity control composition.

In a further embodiment of the present invention, the linearity control composition further comprises a nucleated red blood cell analog for the analysis of nucleated red blood cells. The nucleated red blood cell analogs can be made using methods known in the art. Representative methods for making nucleated red blood cells are described in U.S. Pat. Nos. 5,858,790; 5,648,225, 5,879,900, 6,187,590; 6,200,500; 6,221,668; 6,406,915; 6,406,915; 6,448,085; 6,653,137, 6,723,563; and Patent Application Publication No. US2003/0104631 which are herein incorporated by reference in their entirety. Like the platelet analog and reticulocyte analog concentrations, the nucleated blood cell analog concentration preferably increases with the increase of concentration of the white blood cell analogs, but could also decrease with the increase of other components in the linearity control composition so that an excessively high total particle count is avoided in the linearity control composition.

One suitable example of the suspension medium includes phosphate buffered saline solution and optionally including an aqueous solution of a plasma substance. As defined herein, an aqueous solution of a plasma substance comprises an aqueous solution of a serum substance, serum substance in combination with a plasma protein, and mixtures thereof. As further defined herein, plasma protein comprises one or more of the proteins contained in plasma. Preferably, such plasma proteins include albumin, lipoproteins, globulins, fibrinogens, and mixtures thereof. These media will contain other ingredients known to those skilled in the art to confer long term stability. Example 4 provides two sample formulas of the suspension medium. Other examples of suitable medium are more fully described in U.S. Pat. Nos. 4,213,876, 4,299,726, 4,358,394, 3,873,467, 4,704,364, 5,320,964, 5,512,485, and 6,569,682, which are herein incorporated by reference in their entirety.

Examples 1 and 2 provide illustrative processes of preparing the white blood cell analogs used for the linearity control composition of the present invention. In Example 1, the white blood cell analog is a monocyte analog when measured by impedance as taught by U.S. Pat. No. 4,704,364 (to Carver et al). In Example 2, the white blood cell analog is a lymphocyte analog when measured by VCS measurement as taught by U.S. Pat. No. 5,320,964 (to Young et al). Example 3 provides an illustrative process of preparing a platelet analog used in the linearity control composition. Moreover, Example 5 provides an illustrative process for making stabilized red blood cells that can be used in the linearity control composition.

It has been found that the linearity control composition of the present invention containing white blood cell analogs, stabilized red blood cells and optionally platelet analogs at the high concentrations described above have both open and closed vial stabilities substantially equivalent to the existing reference controls that have the cellular particle concentrations equivalent to normal human blood samples. More specifically, the instant linearity control composition containing white blood cell analogs at a concentration greater than $120 \times 10^3$ analogs per microliter has a closed vial stability of more than 120 days when stored at 2 to 8° C., and an open vial stability of more than 30 days when stored at 2 to 8° C.

In a further aspect, the present invention provides a linearity control system that comprises a series of linearity control compositions described above, wherein the concentration of the white blood cell analogs in the series increases in a range from $0.2 \times 10^3$ to $800 \times 10^3$ analogs per microliter, and the concentration of the stabilized red blood cells is in a range from $0.1 \times 10^6$ to $9 \times 10^6$ cells per microliter. In the linearity control system, at least one, preferably at least two, of the control compositions contains white blood cell analogs at a concentration greater than $120 \times 10^3$ analogs per microliter. Each of the linearity control compositions is prepackaged in a container such as a tube or vial.

In one embodiment, the linearity control system comprises a series of 14 or less, preferably 12 or less, and more preferably 10 or less prepackaged linearity control compositions described above, which are sufficient for determining linearity of enumerations of red blood cells, white blood cells, and platelets. As can be appreciated, testing linearity of several reportable parameters on a hematology analyzer can be time consuming for the operator and it detracts from the time available for using the instrument for diagnostic analysis of real blood samples. Therefore, the linearity control system preferably includes a minimum number of the linearity control compositions that need to be tested to verify the reportable range of the instrument and linearity of the measurements. Moreover, preferably each linearity control composition integrates a maximum number of components that need to be measured for the linearity analysis. However, it is contemplated that the linearity control system can optionally include one or more single component control compositions prepackaged in one or more vials, and the linearity of one or more parameters corresponding to the single components can be determined using these additional single component compositions. The additional single component control composition may further provide flexibility to the linearity analysis, as shown in Table 1 and further described below.

An example of the linearity control system of the present invention is illustrated in Table 1. The first column on the left indicates the level of a specific control composition within the linearity control system. The remaining columns show the manufacturing target concentrations of each component in this series of linearity control compositions. The concentration of each component is expressed with their corresponding reportable parameter in the same unit reported on hematology analyzers. More specifically, the concentration of white blood cell analogs is expressed as WBC in $\times 10^3$ per microliter, the concentration of stabilized red blood cells is expressed as RBC in $\times 10^6$ per microliter, the concentration of platelet analogs is expressed as Plt in $\times 10^3$ per microliter, and hemoglobin concentration is expressed as Hgb in g/dl.

As shown in Table 1, in this exemplary embodiment the linearity control system comprises a series of 11 linearity control compositions, more specifically from Level 1 through Level 11. Optionally, Level 0 is included, which does not contain any cellular particles. Level 0 is used to assess or establish the background of a measurement. As can be appreciated, although a thorough cleaning cycle is performed after analysis of each sample, including blood sample, calibrator or reference control, by the hematology analyzer, there are always a number of residual particles present in the fluid counting system. This is commonly referred to as "carry-over", which is the background in the measurement of a specific parameter. Depending on the reagents used and the fluid system designs, the backgrounds are different on different hematology analyzers and different for different parameters that are measured. For customer convenience, the linearity control system shown in Table 1 includes a medium vial indicated as Level 0, which typically contains the suspension medium used in Levels 1 to 11. It can be understood that other aqueous solutions which do not contain cellular particles can also be used for the same purpose, for example, a filtered saline. Level 0 is run first to assess the background of the measurement of which the linearity is to be determined. If the background of any measurement exceeds an expected limit, cleaning or other maintenance actions has to be taken prior to starting the test of linearity.

TABLE 1

An Example Configuration of The Linearity Control System

| | Components | | | |
|---|---|---|---|---|
| Level | WBC ($\times 10^3$/µl) | RBC ($\times 10^6$ µl) | Hgb (g/dl) | Plt ($\times 10^3$ µl) |
| 0* | 0 | 0 | 0 | 0 |
| 1 | 0.8 | 0.80 | 2.2 | 36 |
| 2 | 1.7 | 1.76 | 5.0 | 64 |
| 3 | 30.0 | 3.00 | 9.0 | 300 |
| 4 | 70.0 | 5.80 | 19.5 | 700 |
| 5 | 80.0 | 6.40 | 20.0 | 770 |
| 6 | 90.0 | 8.00 | 24.0 | n/a |
| 7 | 185.0 | (4.00) n/a | n/a | 1850 |
| 8 | 290.0 | (3.20) n/a | n/a | 2350 |
| 9 | 375.0 | (3.00) n/a | n/a | 2750 |
| 10 | 475.0 | (4.60) n/a | n/a | 0 |
| 11 | 0 | 0 | 0 | 4750 |
| 12* | 0 | 0 | 0 | 0 |

*Medium only

Optionally, Level 12 is also included, which contains only the suspension medium and is merely used to clean the system after analyzing the control compositions of the system. Similar to Level 0, other aqueous solutions which do not contain cellular particles can also be used for the same purpose.

In the linearity control system shown in Table 1, the linearity control compositions from Level 1 to Level 10 are integrated control compositions, each of them containing two to three components. Level 11 is a single component control composition, which is used solely for assessing an upper range of the platelet measurement on the hematology analyzer.

As shown in Table 1, the white blood cell analog concentration increases consecutively from Level 1 to Level 10. From Levels 7 to 10 the white blood cell analog concentrations are greater than $120 \times 10^3$ analogs per microliter.

As can bee appreciated, the function of the stabilized red blood cells in the linearity control system can be divided into two portions. The first portion is from Levels 1 through 6, wherein the concentration of stabilized red blood cells increases consecutively. In this portion, the stabilized red blood cells are mainly used for determining the linearity of red blood cell enumeration and measurement of hemoglobin concentration, although they also aid in dispersion of white blood cell analogs. As shown, the measurement is in a range from 0 to $8\times10^6/\mu l$ for RBC, and from 0 to 24 g/dl for Hgb, respectively. The second portion is from Levels 7 through 10. In this portion, the stabilized red blood cells are merely used for aiding in dispersion of white blood cell analogs. As shown, the concentrations of the stabilized red blood cells in Levels 7 through 10 duplicate or overlap with those in Levels 3 through 6, and they are only shown in parenthesis for the purpose of discussion herein. On the assay sheet of the linearity control system, the assay parameters for RBC and Hgb for Levels 7 through 10 are not provided (n/a). Similarly, Level 6 can optionally include platelet analogs, but as shown in Table 1, the platelet assay parameter is not provided.

It is noted that the concentrations shown in Table 1 are merely for illustrative purposes and representing a manufacturing target. The concentrations of each component of the linearity control compositions typically have a manufacturing tolerance range. The assay parameters are assigned for each lot of the control compositions as described in more detail hereinafter.

The linearity control system can be configured to comprise different combinations of the individual linearity control compositions. Another example of the linearity control system is shown in Table 2. Similar to the first example shown in Table 1, Level 0 is a medium vial, which does not contain any cellular particles, and is used to establish the background of the measurements. Level 10 is used to clean the system after analyzing the other levels of the linearity control system. Similarly, n/a means no assay parameter is provided.

In the linearity control system shown in Table 2, the linearity control compositions from Level 1 through 9 are all integrated control compositions, each containing two to three components. In this system, Levels 7 through 9 contain white blood cell analogs at a concentration greater than $120\times10^3$ analogs per microliter. The concentration of the stabilized red blood cells in Levels 7 though 10 is greater than $2\times10^6$ cells per microliter.

TABLE 2

Another Example Configuration of the Linearity Control System

| Level | WBC ($\times10^3/\mu l$) | RBC ($\times10^6 \mu l$) | Hgb (g/dl) | Plt ($\times10^3 \mu l$) |
|---|---|---|---|---|
| 0* | 0 | 0 | 0 | 0 |
| 1 | 0.8 | 0.80 | 2.2 | 36 |
| 2 | 1.7 | 1.76 | 5.0 | 64 |
| 3 | 30.0 | 3.00 | 9.0 | 300 |
| 4 | 70.0 | 5.80 | 19.5 | 700 |
| 5 | 80.0 | 6.40 | 20.0 | 770 |
| 6 | n/a | 8.00 | 24.0 | n/a |
| 7 | 185.0 | n/a | n/a | 1850 |
| 8 | 290.0 | n/a | n/a | 2350 |
| 9 | 375.0 | n/a | n/a | 2750 |
| 10* | 0 | 0 | 0 | 0 |

*Medium only

It can be appreciated that the number of linearity control compositions in the linearity control system can vary depending upon the measurement ranges of the instrument to be tested. For example, for a hematology analyzer capable of measuring white blood cells up to $200\times10^3/\mu l$, the linearity control system may contain one or two linearity control compositions having white blood cell analog concentration greater than $120\times10^3$ analogs per microliter. However, for a hematology analyzer capable of measuring white blood cells up to $500\times10^3/\mu l$, the linearity control system may contain more than two linearity control compositions having white blood cell analog concentration greater than $120\times10^3$ analogs per microliter.

The linearity control system shown in Tables 1 and 2 can be provided as a control kit. However, the linearity control system can also be provided in more than one kit to test the entire range of the instrument. For example, the linearity control system can comprise one kit of linearity control compositions to test and verify the normal blood concentration range of the reportable parameters; and another kit of linearity control compositions to test and verify the reportable parameters in the concentration ranges of abnormal blood samples measured on the instrument. The linearity control system can also be configured to only test the extended operating range of the instrument. For example, a linearity control system can only include Levels 7 though 9 of Table 2 for determining linearity of extended white blood cell enumeration beyond $100\times10^3/\mu l$.

Example 6 provides an illustrative process of preparing the linearity control system. As shown, after all individual linearity control compositions are prepared and packaged into control vials, the control vials are labeled to indicate their levels in the linearity control system. Then, assay parameters are assigned to the linearity control compositions at each level. The term "assay parameter" used herein includes assay value and target range. Typically, the assay value is provided as a single number with an error range; and the target range is provided as acceptable upper and lower limits. For example, the assay parameter for WBC of Level 8 in the linearity control system shown in Table 2 can be either an assay value of 290±21.6, or a target range with an upper limit of 311.60 and a lower limit of 268.4.

The standard procedures known in the art for assay value assignment of hematology controls are used for the linearity control system. The assay value of a reportable parameter for each lot product is the mean of multiple tests, typically more than 10, of one control composition on one or more designated calibrated hematology analyzers. The error range corresponds to the coefficient of variation (CV) of the specific reportable parameter at the concentration tested. It is noted that the CV varies depending on the concentrations and instruments. The target range for each level is determined using the mean and the CV for each lot of the linearity control composition product.

It can be understood that the assay parameters can be assigned for a specific target hematology analyzer, for example, for Coulter LH750 hematology analyzer, which is a high end product and has higher accuracy and precision than mid range and low end analyzers. In this case, the CV for the reportable parameters, such as WBC and RBC, is relatively small. However, commonly each hematology analyzer manufacturer produces various models of hematology analyzers, from the high throughput products for hospitals to the low end products for doctor's office, and all of these instruments need periodical assessments of linearity of the reportable parameters. To meet such a need, the assay parameters can also be assigned for a group of different hematology analyzers. In this situation, the error ranges for the assay value are larger and the target range is broader, because the highest CV among these different instruments will dominate. Moreover, the acceptable limits for backgrounds of the measurements are typically higher due to the same reason.

Table 3 provides an example assay sheet of the linearity control system of the present invention. The target ranges assigned (indicated as Expected Results) in this exemplary embodiment can be used for determining linearity of several hematology analyzers manufactured by Beckman Coulter, Inc. (Fullerton, Calif.). As shown, this embodiment of the linearity control system comprises nine linearity control compositions, from Level 1 to Level 9, and further comprises a medium vial, Level 0.

TABLE 3

Example Assay Sheet of A Linearity Control System

| | Expected Results (Upper and Lower Limits) | | | |
|---|---|---|---|---|
| Level | WBC ($\times 10^3/\mu l$) | RBC ($\times 10^6 \mu l$) | Hgb (g/dl) | Plt ($\times 10^3 \mu l$) |
| 0 | 0.0-0.4 | 0.00-0.03 | 0.0-0.4 | 0-5 |
| 1 | 0.4-1.2 | 0.56-0.94 | 1.7-2.5 | 26-46 |
| 2 | 1.1-2.1 | 1.54-1.94 | 4.3-5.3 | 49-81 |
| 3 | 25.4-37.4 | 2.69-3.39 | 9.1-10.5 | 245-375 |
| 4 | 63.4-79.4 | 5.41-6.21 | 17.2-20.2 | 532-852 |
| 5 | 72.7-96.7 | 5.96-6.96 | 19.2-22.6 | 606-956 |
| 6 | n/a | 7.52-8.32 | 22.7-26.5 | n/a |
| 7 | 170.1-215.9 | n/a | n/a | 1451-2213 |
| 8 | 288.0-331.2 | n/a | n/a | 1794-2774 |
| 9 | 346.6-420.8 | n/a | n/a | 2033-3389 |

It is noted that in Level 0 the upper limit for each of these reportable parameters reflects the highest acceptable background observed among all instruments that the linearity can be tested using this linearity control system. However, typically a high end product has substantially lower background than the upper limits for Level 0 shown in the table, for example, the background can be less than $0.1 \times 10^3/\mu l$ for WBC and less than $0.01 \times 10^6/\mu l$ for RBC. Consequently, for the hematology analyzers having lower backgrounds the concentrations of the white blood cell analogs, the stabilized red blood cells and the platelet analogs in the control composition of Level 1 can be extended to the extreme low end of the reportable range, for example, $0.2 \times 10^3$ analogs per microliter for the white blood cell analogs, and $0.1 \times 10^6$ cells per microliter for the stabilized red blood cells. It is noted that linearity of the measurements at the extreme low end is important for analysis of clinical body fluid samples, which typically have very low particle counts.

As shown in Table 3 and described previously with the embodiment shown in Table 1, not all of the linearity control compositions have an assay parameter for each of the four reportable parameters (WBC, RBC, Hgb and Plt). However, to ensure a sufficient number of linearity control compositions being used for determining linearity of each reportable parameter, in the linearity control system at least five, preferably at least six, of the linearity control compositions have assigned assay parameters for white blood cell count (WBC), at least five, preferably at least six, of the linearity control compositions have assigned assay parameters for red blood cell count (RBC) and hemoglobin concentration (Hgb), and at least five, preferably at least six, of the linearity control compositions have assigned assay parameters for platelet count (Plt).

In addition to the assay sheet described above, optionally, a graph paper in linear scale can also be enclosed in the control kit for the customers to plot the report values and assay parameters for determining the linearity of one or more measurements.

In another aspect, the present invention provides a method of verifying the reportable measurement range and linearity of white blood cell enumeration over an extended concentration range on a hematology analyzer using multiple instant linearity control compositions containing white blood cell concentrations. More specifically, the method uses a series of linearity control compositions, each thereof comprising a predetermined concentration of white blood cell analogs, a predetermined concentration of stabilized red blood cells and a suspension medium, wherein the concentration of the white blood cell analogs in the series of control compositions increases in a range from $0.2 \times 10^3$ to $800 \times 10^3$ analogs per microliter, and in at least one, preferably two or more, of the control compositions the concentration of the white blood cell analogs is greater than $120 \times 10^3$ analogs per microliter. When the concentration of the white blood cell analogs exceeds $120 \times 10^3$ analogs per microliter, the concentration of the stabilized red blood cells is at least $1.5 \times 10^6$, and preferably greater than $2 \times 10^6$ cells per microliter.

The method of measuring high concentration of white blood cells in abnormal samples has been described in U.S. Pat. No. 6,744,245, which is hereby incorporated by reference in its entirety. As illustrated in U.S. Pat. No. 6,744,245, using such a method the white blood cell concentration (WBC) is measured linearly up to a concentration of $500 \times 10^3/\mu l$ with a DC impedance measurement using a non-focus flow aperture. Using a focused flow cell, the upper range of the enumeration can be further extended substantially.

When practicing the method of the present invention, the linearity control compositions are gently mixed to disperse the white blood cell analogs in the suspension medium in the prepackaged control vials, as described in detail above. As described previously, the mixing time of the linearity control compositions of the present invention is less than 90 seconds for mixing one control vial. Typically, the mixing time is less than 50 seconds, and preferably less than 40 seconds. Commonly, following the manual mixing procedure described in Example 7 the mixing time for individual control vials is about 20 to 30 seconds. Therefore, the total time used for mixing all control vials of the linearity control system containing less than 14 individual linearity control compositions is typically less than 15 minutes. No manual dilution of the linearity control composition is required, and no vortex or other vigorous mixing is used for achieving mono-dispersion of the analogs and cells in the control compositions.

The white blood cell enumeration of an instrument is considered linear and operating within manufacturer's specifications, if the means of the report values at all levels of the linearity control system are within the target ranges, or error ranges of the assay values, provided by the manufacturer. The report values are also commonly referred to as recovered values. As can be appreciated by those ordinary skilled in the art, the linearity control system of the present invention can also be used for verification of precision and bias of white blood cell enumeration of the instrument.

In a further aspect, the present invention provides methods of using the linearity control system of the present invention for verifying the reportable measurement range and determining linearity of measurements of several reportable parameters on the hematology analyzer.

In one embodiment, a method is provided for determining the linearity of the enumerations of white blood cells and red blood cells over extended concentration ranges using the linearity control system of the present invention, wherein the concentration of the white blood cell analogs in the series of control compositions increases in a range from $0.2 \times 10^3$ to $800 \times 10^3$ analogs per microliter, and in at least one, preferably two or more, of the control compositions the concentration of the white blood cell analogs is greater than $120 \times 10^3$ analogs per microliter. The concentration of the stabilized red blood cells is in a range from $0.1 \times 10^6$ to $9 \times 10^6$ cells per microliter.

In a further embodiment, the present invention provides a method for determining the linearity of enumerations of the white blood cells, red blood cells, and platelets over extended concentration ranges using the linearity control system of the present invention. In addition to the high concentrations of white blood cell analogs and the stabilized red blood cells described immediately above, in this embodiment, at least one, preferably at least two, of the linear control compositions comprises platelet analogs at a concentration greater than $1,400 \times 10^3$ analogs per microliter.

More specifically, the method comprises the following steps:

(a) providing a series of control compositions, each of the control compositions comprising a predetermined concentration of white blood cell analogs, stabilized red blood cells in a concentration range from about $0.1 \times 10^6$ to about $9 \times 10^6$ cells per microliter, platelet analogs in a concentration up to $7,000 \times 10^3$ analogs per microliter, and a suspension medium; the concentration of the white blood cell analogs in the series of control compositions increasing in a range from $0.2 \times 10^3$ to $800 \times 10^3$ analogs per microliter and in at least one, preferably at least two of the control compositions greater than $120 \times 10^3$ analogs per microliter; at least five of the control compositions having assay parameters of white blood cell count, and at least five of the control compositions having assay parameters of red blood cell count and hemoglobin concentration, and at least five of the control compositions having assay parameters of platelet count;

(b) gently mixing the control compositions to disperse the analogs and the cells in the suspension medium;

(c) analyzing each of the control compositions on a hematology analyzer, and obtaining report values of the white blood cell count, the red blood cell count, and the platelet count of each of the control compositions; and (d) determining linearity of enumerations of the white blood cells, the red blood cells, and platelets of the hematology analyzer using the report values and the assay parameters of the control compositions.

The method further comprises determining linearity of the measurement of hemoglobin concentration, wherein in step (c) the analysis further includes measuring hemoglobin concentration of each of the control compositions; and subsequently determining linearity of hemoglobin measurement using the report values of hemoglobin concentration and assay parameters for hemoglobin concentration of the control compositions.

As understood by those skilled in the art, the measurement of the components of the linearity control composition in an automated hematology analyzer can occur using one or more aliquots of the control composition, typically in the same manner of the analysis of blood samples. For example, without limiting the scope of the invention, reference is made to the Coulter GEN*S™ or LH750 hematology analyzer (Beckman Coulter, Inc., Fullerton, Calif.). In each of these automated hematology analyzers, several aliquots of a blood sample or a reference control are processed separately and analyzed concurrently in different analysis modes for measurement of different blood cell subpopulations. More specifically, a first aliquot of a blood sample is diluted by a blood diluent to form a first sample mixture, and red blood cells and platelets are measured by DC impedance measurement to obtain red blood cell and platelet parameters, including red blood cell count, platelet count and numerous other parameters. At the same time, a second aliquot of the blood sample is mixed with a blood diluent and a first lytic reagent to form a second sample mixture. The second sample mixture is measured by a DC impedance measurement and a spectrophotometric measurement at a predetermined wavelength to obtain the white blood cell count, to differentiate white blood cells into three subpopulations and differentiate nucleated red blood cells, and to obtain hemoglobin concentration. A third aliquot of the sample is mixed with a second lytic reagent, and subsequently is mixed with a stabilizing reagent to form a third sample mixture. The third sample mixture is delivered to a focused flow cell and is measured by the VCS detection method to differentiate white blood cells into five subpopulations and to differentiate nucleated red blood cells. Additionally, a fourth aliquot of the sample is exposed to a reticulocyte reagent system to form a fourth mixture, which is measured by the VCS detection method to analyze reticulocytes.

The term of "VCS measurement or detection method" used herein refers to a three-dimensional measurement technology which measures the direct current (DC) and radio frequency (RF) impedances, and light scatter signals of a blood cell when it passes through a flow cell. The VCS detection method has been described in detail in U.S. Pat. No. 5,125,737, which is hereby incorporated by reference in its entirety.

Example 7 provides an illustrative process of using the linearity control system for determining the linearity of enumerations of white blood cells, red blood cells and platelets, and the hemoglobin measurement. As shown, the control vials are mixed by hands following a procedure that has been used for many years in clinical laboratories for handling reference controls containing cellular particles at concentrations equivalent to those in the normal blood samples. Using this procedure, the control vials are gently mixed by hands within tens of seconds, without any vigorous mixing. Moreover, all levels of the control compositions are used directly on the instrument, without further dilution by the operator.

After obtaining the report values of WBC, RBC, Hgb and Plt for each level of the linearity control system and obtaining the mean of the report values for each of these four parameters, the linearity of the measurement for each of these reportable parameters can be determined graphically as illustrated in Example 7, or numerically with reference to the target ranges provided in the assay sheet. The enumeration of a specific blood cell population of the instrument is considered linear and operating within manufacturer's specifications, if the means of the report values at all levels of the linearity control system are within the target ranges, or error ranges of the assay values, provided by the manufacturer.

As shown in Example 6, for customer convenience a graph paper in linear scale can be provided in the control kit, together with the assay sheet. The operator can simply plot the target ranges of a reportable parameter, such as WBC, for each available level provided in the assay sheet on the graph paper and plot the means of the report values of each corresponding level. If the means fall within the target ranges for all levels, the result indicates that the enumeration of white blood cells on the tested hematology analyzer is linear.

Alternatively, a linear regression analysis, or other statistical analyses, can be performed to assess the linearity of the measurements of each of these four parameters. Furthermore, linearity of the enumerations can be further assessed by determining whether any trending exists within the tested concentration range.

Figure 1:
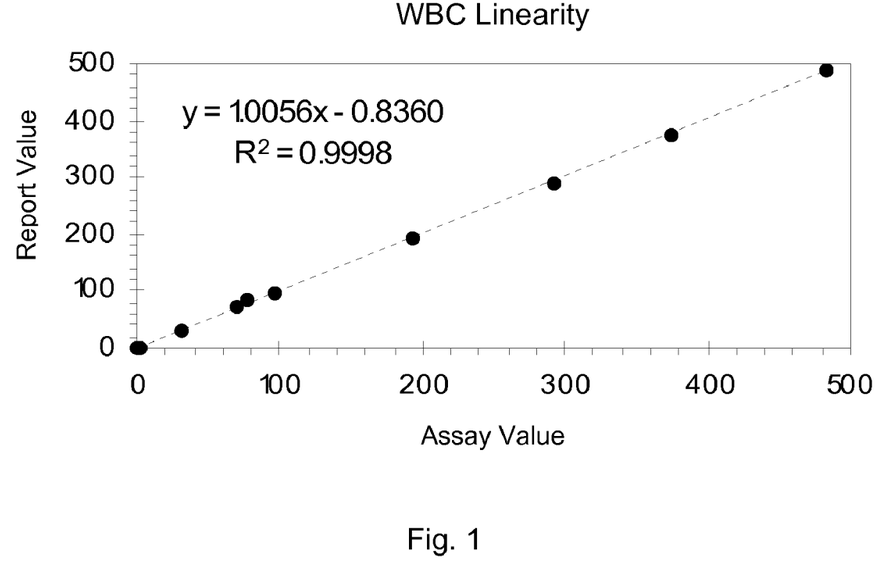
FIG. 1 illustrates a representative graph showing the linearity determination result of the white blood cell enumeration of a hematology analyzer using the linearity control system of the present invention.
Figure 2:
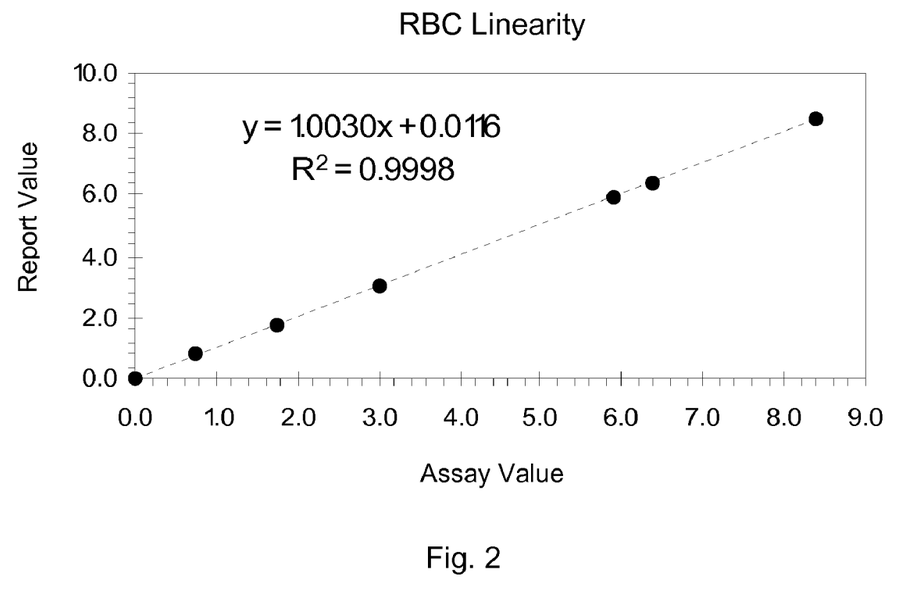
FIG. 2 illustrates a representative graph showing the linearity determination result of the red blood cell enumeration of a hematology analyzer using the linearity control system of the present invention.
Figure 3:
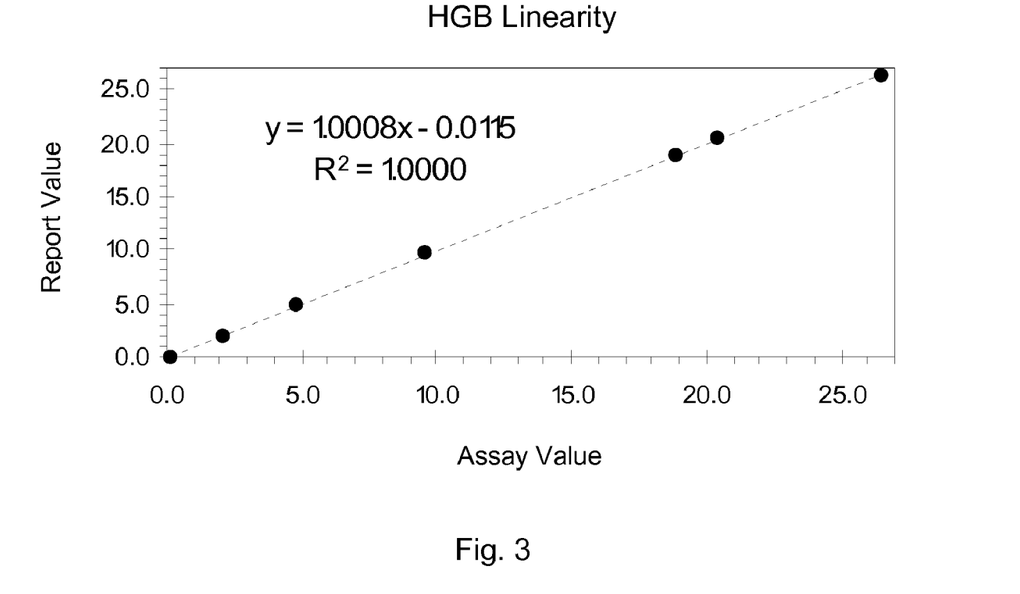
FIG. 3 illustrates a representative graph showing the linearity determination result of the platelet enumeration of a hematology analyzer using the linearity control system of the present invention.
Figure 4:
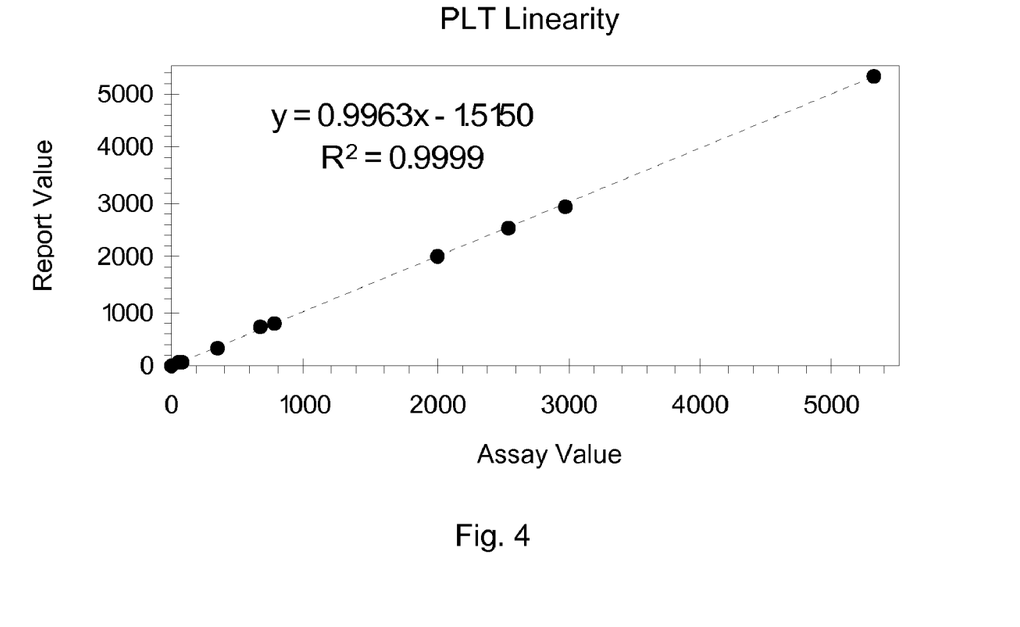
FIG. 4 illustrates a representative graph showing the linearity determination result of the hemoglobin measurement of a hematology analyzer using the linearity control system of the present invention.

FIGS. 1-4 show a set of representative graphs illustrating the linearity determination results for the enumerations of white blood cells, red blood cells and platelets, and the hemoglobin measurement of a Coulter LH750 hematology analyzer using the linearity control system of the present invention and the procedure described in Example 7.

In yet a further embodiment, the present invention provide a method for determining linearity of the enumerations of white blood cells, red blood cells, platelets, reticulocytes and nucleated red blood cells, and the measurement of hemoglobin concentration over extended concentration ranges using the linearity control system of the present invention. In this embodiment, the linearity control compositions further comprises reticulocyte analogs and nucleated red blood cell analogs, in a concentration range corresponding to those observed in clinical abnormal blood samples.

The method of measuring reticulocytes using VCS measurement has been described fully in U.S. Pat. Nos. 5,492,833, 5,616,501 and 6,060,322, which are hereby incorporated by reference in their entirety. The methods of measuring nucleated red blood cells in a blood sample have been described fully in U.S. Pat. Nos. 5,874,310, 5,917,584, 6,410,330, 6,472,215, 6,673,618, 7,008,792 and 7,208,319, which are hereby incorporated by reference in their entirety.

It should be understood that the present invention is not limited to being used with the methods provided above, and can be used with other measurement methods known to those skilled in the art including those using one or more measurements of impedance, radio frequency, light scatter, axial light loss, and fluorescence measurements. Naturally, a limited amount of experimentation might be required to optimize the present invention for such other measurement methods.

The following examples are illustrative of the invention and are in no way to be interpreted as limiting the scope of the invention, as defined in the claims. It will be understood that various other ingredients and proportions may be employed, in accordance with the proceeding disclosure.

Example 1

White Blood Cell Analogs Made of Goose Red Blood Cells

The following is one example of preferred reagents and recommended specific procedural steps for treating geese red blood cells to obtain the white blood cell analog for the linear control composition. It is understood that the formulations and the procedures are only illustrative and that other ingredients, proportions and procedures may be employed, in accordance with the disclosures in this invention.

(1) Anticoagulants for Collection of Whole Blood

One or more of the following anticoagulants can be used in a suitable quantity, as determined by one skilled in the art.

(a) Standard ACD (acid-citrate-dextrose)
(b) Standard CPD (citrate-phosphate-dextrose)
(c) Disodium EDTA (ethylenediamine tetraacetate), 2 mg/ml of blood.

(2) Goose Erythrocyte Washing and Diluting Solution

| Goose Erythrocyte Washing and Diluting Solution (GEWDS) | |
| --- | --- |
| Component | Amount (g/l) |
| Sodium phosphate monobasic | 1.31 g |
| Sodium phosphate dibasic | 10.35 g |
| Sodium chloride | 2.50 g |
| Potassium chloride | 0.3 g |
| q.s. to 1 liter with distilled water | |
| pH approximately 7.3 | |
| Osmolality 200 mOsm/kg $H_2O$ | |

(3) Washing and Resuspending Solution for Fixed Cells

| Fresh Blood Wash Solution and Washing and Resuspending Solution for Fixed Cells (WRS) | |
| --- | --- |
| Component | Amount (g/l) |
| Sodium phosphate monobasic | 0.2 g |
| Sodium phosphate dibasic $7H_2O$ | 2.0 g |
| Sodium azide | 0.1 g |
| Sodium chloride | 9.4 g |
| q.s. to 1 liter with distilled water | |
| pH approximately 7.4 | |
| Osmolality 315 to 345 mOsm/kg $H_2O$ | |

(4) White Blood Cell Analog Preparation Procedure

1. Centrifuge goose fresh whole blood at 700 RCF for 10 minutes at ambient temperature. Remove the supernatent along with the buffy coat carefully, without disturbing the packed red blood cells.

2. Wash goose red blood cells two times with 4 to 10 volumes of GEWDS using centrifugation.

3. Dilute the packed red blood cells with GEWDS and measure out a 2 ml sample for determination of red blood cell count and mean cell volume, which should be approximately $0.33 \times 10^6/\mu l$ and 155 fl, respectively.

4. Prepare a glutaraldehyde fixing reagent having a glutaraldehyde concentration of about 1.0 to 10.0% by adding a commercial 25% glutaraldehyde product to the GEWDS. A preferred glutaraldehyde concentration is 5%.

5. Add 1 volume of the glutaraldehyde fixing reagent to 9 volumes of the washed red blood cell suspension from step (3), and mix thoroughly for about 3 to 4 minutes. Transfer to sealed containers which are rolled slowly for 20 to 28 hours.

6. Centrifuge the fixed red blood cells at about 400 RCF for 5 minutes. Remove the supernatant fluid and wash several times with WRS, which result in the white blood cell analogs.

7. For a linearity control composition, resuspend the washed fixed red blood cells in a suitable storing solution or the suspension media of Example 4 and adjust the concentration of white blood cell analogs to the desired concentration taking into consideration the additional volume of stabilized red blood cells.

Example 2

White Blood Cell Analog Made of Avian Red Blood Cells

The following is a specific example of preferred reagents and recommended procedural steps for treating goose red blood cells to obtain a normal sized lymphocyte analog. The white blood cell analogs made using this method can be used as lymphocyte analogs using VCS measurement, and they are used as the white blood cell analogs for the linearity control composition of the present invention. It will be understood that the formulations and the procedures only are illustrative and that other ingredients, proportions and procedures can be employed, in accordance with the disclosures in this invention.

| Lymphocyte Hypotonic Solution | |
|---|---|
| Component | Amount (g/l) |
| Sodium phosphate monobasic | 0.2 g |
| Sodium phosphate dibasic 7H$_2$O | 2.0 g |
| q.s. to 1 liter with distilled water | |
| pH approximately 7.8 | |
| Osmolality 15 to 25 mOsm/kg H$_2$O | |

White blood cell analog preparation procedure

1. Select goose red blood cells having a mean cell volume range of about 140 to about 170 fl. Wash the packed goose red blood cells with the phosphate buffered saline solution (PBS) described in Example 1.

2. Add 1.0 to 5.0 milligrams of cholesterol to a cell count of 2×10$^6$ per microliter and incubate for 2 to 6 hours, at room temperature.

3. Prepare a glutaraldehyde fixing reagent having a glutaraldehyde concentration of about 0.1 to 0.8% by adding a commercial 25% glutaraldehyde product to the chilled Lymphocyte Hypotonic Solution. Preferably, the temperature is from 2° C. to 8° C. The preferred concentration of glutaraldehyde is approximately 0.35%.

4. Add the washed red blood cells to a measured amount of the fixing reagent of step 3 at a 1:35 dilution. Transfer to sealed containers which are rolled slowly for 18 to 24 hours at 2° C. to 8° C. The reduction in hemoglobin content is calculated to be approximately 60% by weight.

5. Remove the supernatant fluid, wash cells several times with the PBS, then suspend in a suitable storing solution or the suspension media of Example 4, which result in the white blood cell analogs.

6. For a linearity control composition, suspend the washed fixed red blood cells in the Suspension Media of Example 4 and adjust the concentration of white blood cell analogs to the desired concentration taking into consideration the additional volume of stabilized red blood cells.

Example 3

Method of Making a Platelet Analog

Platelet Analog Preparation Procedure

1. Obtain fresh goat whole blood with an MCV of 12 to 16 fl.

2. Wash the red blood cells with a phosphate buffered saline to remove unwanted cellular components, such as white blood cells, platelets, plasma, and plasma proteins.

3. The washed goat red blood cells are suspended in Suspension Medium 2 of Example 4 at a known cell count.

Example 4

Illustrative Formulations of the Suspension Media

Following suspension media were prepared and used for the linearity control compositions of the present invention.

| Suspension Medium 1 | | |
|---|---|---|
| Component | Range (g/l) | Preferred Range (g/l) |
| Xanthine compound | 1-10 | 2-7 |
| Adenosine monophosphate | 0.1-1.0 | 0.2-0.8 |
| Inosine | 0.1-1.0 | 0.2-0.8 |
| pH adjusting agents sufficient to obtain | pH 5.8-6.8 | pH 6.0-6.5 |
| Osmolarity adjusters sufficient to obtain | 200-400 mOsm | 250-350 |
| Preservative | effective amount | 2.0-6.0 |
| q.s. to 1 liter with deionized water | | |

| Suspension Medium 2 | |
|---|---|
| Component | Preferred Range (g/l or ml/l) |
| Propyl paraben | 0.3 to 1.0 g |
| Methyl paraben | 0.5 to 1.0 g |
| Procaine hydrochloride | 0.1 to 0.5 g |
| Deoxycholic acid | 0.1 to 0.9 g |
| Lactose | 10.0 to 50.0 g |
| Actidione | 0.1 to 0.6 g |
| Trisodium citrate dehydrate | 3.0 to 8.0 g |
| Citric acid monohydrate | 0.3 to 0.9 g |
| Sodium dihydrogenphosphate monohydrate | 0.8 to 2.5 mg |
| Phenergan hydrochloride | 0.1 to 1.0 g |
| Colistimethate, sodium | 0.2 to 0.9 g |
| Penicillin G., sodium | $0.5 \times 10^6$ to $3 \times 10^6$ units |
| Kanamycin sulfate | 0.2 to 0.8 g |
| Neomycin sulfate | 0.2 to 1.0 g |
| 5'-AMP | 0.4 to 1.0 g |
| Adenine | 0.2 to 0.8 g |
| Inosine | 0.4 to 1.0 g |
| Dihydrostreptomycin sulfate | 0.2 to 1.0 g |
| Tetracycline hydrochloride | 0.2 to 1.0 g |
| 30% Bovine albumin | 100 to 350 ml |
| q.s. to 1 liter with deionized water | |

Example 5

Method of Making Stabilized Red Blood Cells

Preparation Procedure 1:

1. Whole human or animal blood was first centrifuged to obtain packed red blood cells.

2. Then the packed red blood cells were suspended in a preconditioning diluent as shown below. The preconditioning of the red blood cells in the preconditioning diluent was preferably accomplished at 22° C. to 27° C. for a time period of 48 hours. This process reduced cell volume, and stabilizes the cells and size distribution width, prior to their exposure to the suspension media.

3. After preconditioning, the cell suspension can be stored at 4° C. to 6° C. until ready to be mixed with the suspension medium.

4. At such time the preconditioned red blood cells were separated from the diluent, by centrifuging, and mixed with the Suspension Medium of 2 of Example 4.

A preferred formulation of the preconditioning diluent is shown as follows.

| Preconditioning Diluent | | |
|---|---|---|
| Component | Example | Preferred Range |
| Lactose | 90.0 g/l | 25-100 g/l |
| Sodium azide | 1.5 g/l | 0.5-4.0 g/l |
| Trisodium citrate dihydrate | 5.0 g/l | 2.5-5.0 g/l |
| Citric acid monohydrate | 0.1 g/l | 0.05-0.2 g/l |
| Non-ionic surfactant (Pluronic F68) | 1.0 g/l | 0.25-1.5 g/l |
| q.s. to 1 liter with deionized water | 350 mOs/kg | 350-360 mOsm/kg |
| | pH approximately 6.9 | pH range 6.5-7.5 |

Preparation Procedure 2:

1. Whole human or animal blood is first centrifuged to obtain packed red blood cells.

2. The packed red blood cells are washed with a phosphate buffered saline.

3. The washed red blood cells were suspended in Suspension Medium 2 of Example 4.

Example 6

Preparation of a Linearity Control System

Preparation Procedure:

1. Provide a predetermined volume of Suspension Medium 1 or 2 of Example 4.

2. Add a predetermined amount of stabilized human red blood cells in the Suspension Medium. The stabilized human red blood cells were processed using the Preparation procedure 2 shown in Example 5.

3. Add a predetermined amount of platelet analogs in the suspension medium containing the stabilized human red blood cells. The platelet analogs were made of stabilized goat red blood cells as described in Example 3.

4. Add a predetermined amount of white blood cell analogs made of fixed goose red blood cells as described in Example 1 into the suspension medium containing the stabilized human red blood cells and the platelet analogs.

5. Optionally, add a predetermined amount of reticulocyte analogs, a predetermined amount of nucleated blood cell analogs, or both into the suspension medium containing the stabilized human red blood cells, platelet analogs, and white blood cell analogs.

6. Mix the formed linearity control composition gently, fill the linearity control composition into control vials, and store in the closed control vials under refrigeration.

7. Repeat steps 1 through 6 using different combinations of a predetermined amount of each component to form a series of linearity control compositions wherein at least one of the linearity control compositions had a white blood cell analog concentration greater than $120 \times 10^3$ analogs per microliter. This series of linearity control compositions formed the linearity control system.

8. Assign assay values or target ranges for white blood cell count (WBC) to at least five of the linearity control compositions, assign assay values or target ranges for red blood cell count (RBC) and hemoglobin concentration (Hgb) to at least five of the linearity control compositions, and assign assay values or target ranges for platelet count (Plt) to at least five of the linearity control compositions, using standard procedures used for assay value assignment of calibrators and hematology controls. When the target ranges were assigned, the coefficients of variation (CV) of the target hematology analyzers at different particle concentrations were used for assigning the upper limit and lower limit of the target ranges for the linearity control compositions.

9. Label the control vials with indication of their corresponding levels in the linearity control system, package the series of linearity control compositions into a kit, and provide an assay sheet for the linearity control system.

10. Optionally, a graph paper was enclosed in each kit for the customers to plot the report values and assay parameters to the linearity analysis.

Example 7

Using the Linearity Control System to Determine Linearity of Enumerations of White Blood Cells, Red Blood Cells, Platelets and Measurement of Hemoglobin Concentration The linearity control system obtained from Example 6 was used on a Coulter LH750 hematology analyzer (manufactured by Beckman Coulter, Inc., Fullerton, Calif.) to determine the linearity of enumerations of white blood cells, red blood cells and platelets and measurement of hemoglobin concentration of the instrument. The Coulter LH750 hematology analyzer was equipped with a RBC bath using three non-focused flow apertures and a DC-impedance detector for measuring red blood cells; a WBC bath using three non-focused flow apertures and a DC-impedance detector for measuring white blood cell count; and a focused flow cell and a VCS detection system for differential analysis of white blood cells, reticulocytes and nucleated red blood cells.

The measurement of a reference control or a blood sample on the hematology analyzer was as follows. A sample (a blood or a linearity reference control composition) was aspirated by the hematology analyzer. A first aliquot of 1.6 μl of the sample was diluted in the RBC bath by an isotonic blood diluent, LH700 Series Diluent, with a dilution ratio of 6250:1 to form a first sample mixture. The first sample mixture was drawn through the three apertures by a vacuum source. Each blood cell was measured, as it passed through the apertures by the DC impedance detector to obtain red blood cell and platelet parameters. A second aliquot of 28 μl of the sample was diluted in the WBC bath with 6 ml of the LH700 Series Diluent, then mixed with 1 ml of a first lytic reagent, Lyse S® III diff to form a second sample mixture. The second sample mixture was drawn through the three apertures by a vacuum source, and measured for obtaining white blood cell count, differentiating white blood cell into three subpopulations and analyzing nucleated red blood cell. The measurement was performed at a temperature in a range of about 18° to about 28° C. The data obtained from measurements of the second aliquot samples were analyzed to report the white blood cell count and hemoglobin concentration. A third aliquot of the sample was reacted with a second lytic reagent system and measured by the VCS detection system to obtain differentiation of white blood cells and enumeration of nucleated red blood cells. Moreover, a fourth aliquot of the sample was exposed to a reticulocyte reagent system and measured by the VCS detection system to obtain reticulocyte parameters. All reagents described above were products of Beckman Coulter, Inc.

For determination of linearity of enumerations of white blood cells, red blood cells and platelets and measurement of hemoglobin concentration, the following steps were carried out:

(1) The control vials of the packaged linearity control system were removed from the refrigerator and left at ambient room temperature for 15 minutes to warm up.

(2) After warming the control vials, the control vials were mixed by hand as follows:
  a. The control vials were rolled slowly between the palms of the hands eight times in an upright position.
  b. Then, the control vials were inverted and slowly rolled between the palms another eight times.
  c. Subsequently, the control vials were gently inverted eight times.

(3) The contents of the control vials were visually inspected for complete resuspension. If necessary, steps 2a to 2c were repeated until the contents were uniformly suspended.

(4) Perform a startup of the hematology analyzer, the background counts reported at the startup were recorded.

(5) All levels of the linearity control system were analyzed on the hematology analyzer in consecutive order, beginning with Level 0. Each level of the linearity control system was analyzed minimum three times on the analyzer. The flagged runs with non-numeric report were repeated. The report values from a minimum three analysis were used to calculate the mean of the report values.

(6) Record the report values of WBC, RBC, Hgb and Plt for each level of the linearity control system. Calculate the mean of the report values for each of these four parameters.

(7) Plot the target ranges of WBC for each available level provided in the assay sheet on a graph paper in linear scale, and plot the mean of the report values of each corresponding level. If the means fall within the target ranges for all levels, the result indicated that the measurement of WBC on the tested hematology analyzer was linear. This can be easily visualized by drawing a line to connect all means of the report values on the graph paper. The linearity of WBC measurement could be further assessed by determining whether any trending existed within the tested concentration range.

(8) Repeat step (7) for RBC, Hgb and Plt, to assess the linearity of the measurements of RBC, Hgb and Plt on the tested hematology analyzer.

Alternatively, a linear regression analysis, or other statistical analyses, can be performed to assess linearity of the measurement for each of these four parameters.

FIGS. 1-4 show a set of representative graphs illustrating the linearity determination results for the enumerations of white blood cells, red blood cells, platelets, and hemoglobin concentration measurement of a Coulter LH750 hematology analyzer using the instant linearity control system and the procedure described above. The correlation curves were obtained by linear regression analysis using the means of the report values and the assay values for each of the four parameters. It is noted that in this particular example, the linearity control composition containing more than $5,000 \times 10^3$ platelet analogs per microliter was diluted prior to the analysis on the hematology analyzer, because the concentration of the platelet analogs exceeded the limitation of the measurement range of the instrument.

While the present invention has been described in detail, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A linearity control composition comprising:
  a) white blood cell analogs in an elevated concentration greater than $120 \times 10^3$ analogs per microliter;
  b) stabilized red blood cells prepared by washing and suspension in a solution, in a concentration of at least $1.5 \times 10^6$ cells per microliter to facilitate mono-dispersion of said elevated concentration of said white blood cell analogs; and
  c) a suspension medium;
  wherein said elevated concentration of said white blood cell analogs and said red blood cells are capable to be mono-dispersed in said suspension medium by mixing said control composition by manual inversions or rotations, or rotating by a roller, of a vial containing said control composition.

2. The linearity control composition of claim 1 further comprising platelet analogs.

3. The linearity control composition of claim 2 further comprising nucleated red blood cell analogs, reticulocyte analogs, or a combination thereof.

4. The linearity control composition of claim 1, wherein said suspension medium contains a lipoprotein.

5. A linearity control system comprising a series of linearity control compositions; each of said linearity control compositions comprising:
  a) a predetermined concentration of white blood cell analogs;
  b) stabilized red blood cells prepared by washing and suspension in a solution, in a concentration range from $0.1 \times 10^6$ to $9'10^6$ cells per microliter; and
  c) a suspension medium; and
  wherein said concentration of said white blood cell analogs in said series of control compositions increases in a range from $0.2 \times 10^3$ to $800 \times 10^3$ analogs per microliter, and said white blood cell analogs in at least one of said series of control compositions are in an elevated concentration greater than $120 \times 10^3$ analogs per microliter, wherein when said white blood cell analogs in said control compositions are greater than $120 \times 10^3$ analogs per microliter, said concentration of said stabilized red blood cells is at least $1.5 \times 10^6$ cells per microliter to facilitate mono-dispersion of said elevated concentration of said white blood cell analogs; and wherein said elevated concentration of said white blood cell analogs and said red blood cells are capable to be mono-dispersed in said suspension medium by mixing said control compositions by manual inversions or rotations, or rotating by a roller, of vials containing control compositions.

6. The linearity control system of claim 5, wherein said concentration of said white blood cell analogs in at least two of said series of control compositions is greater than $120 \times 10^3$ analogs per microliter.

7. The linearity control system of claim 6, wherein said concentration of said white blood cell analogs in at least one of said series of control compositions is greater than $200 \times 10^3$ analogs per microliter.

8. The linearity control system of claim 5, wherein each of said linearity control compositions further comprises platelet analogs.

9. The linearity control system of claim 8, wherein each of said linearity control compositions further comprises nucleated red blood cell analogs, reticulocyte analogs, or a combination thereof.

10. The linearity control system of claim 5, wherein said suspension medium contains a lipoprotein.

11. The linearity control system of claim 5, wherein each of said control compositions is contained in one of said vials and is used directly on a hematology analyzer after said mixing without manual dilution.

12. The linearity control system of claim 5 further comprising a medium vial containing said suspension medium without cellular particles for establishing background of a measurement of which linearity is to be determined.

13. The linearity control system of claim 12 comprising 14 or less said linearity control compositions.

14. The linearity control system of claim 12 further comprising one or more single component vials containing a single component selected from the group consisting of platelet analogs, said stabilized red blood cells, reticulocyte analogs and nucleated red blood cell analogs.

15. A method of determining linearity of white blood cell enumeration of a hematology analyzer in an extended white blood cell concentration range comprising the steps of:
   (a) providing a series of linearity control compositions; each of said control compositions comprising a predetermined concentration of white blood cell analogs, a predetermined concentration of stabilized red blood cells prepared by washing and suspension in a solution, and a suspension medium; said concentration of said white blood cell analogs in said series of control compositions increasing in a range from $0.2\times10^3$ to $800\times10^3$ analogs per microliter and in at least one of said control compositions said white blood cell analogs being in an elevated concentration greater than $120\times10^3$ analogs per microliter, wherein when said white blood cell analogs in said control compositions are greater than $120\times10^3$ analogs per microliter, said concentration of said stabilized red blood cells is at least $1.5\times10^6$ cells per microliter to facilitate mono-dispersion of said elevated concentration of said white blood cell analogs;
   (b) mixing said control compositions by manual inversions or rotations, or rotating by a roller, of vials containing said control compositions to mono-disperse said elevated concentration of said white blood cell analogs and said stabilized red blood cells in said suspension medium;
   (c) analyzing each of said control compositions on a hematology analyzer, and obtaining report values of white blood cell count for said control compositions; and
   (d) determining linearity of said white blood cell enumeration of said hematology analyzer using said report values and known assay values or known target ranges of said white blood cell count of said control compositions.

16. The method of claim 15, wherein said mixing of said control compositions to disperse said analogs in said suspension medium comprises a mixing time of less than 90 seconds.

17. The method of claim 16, wherein each of said control compositions is contained in one of said vials, and is used directly on said hematology analyzer after said mixing, without a manual dilution.

18. The method of claim 17, wherein said method uses at least two of said control compositions having said concentration of white blood cell analogs greater than $120\times10^3$ analogs per microliter.

19. The method of claim 17, wherein said method further analyzes an aqueous solution not containing cellular particles to establish background of said white blood cell enumeration.

20. A method of determining linearity of enumerations of red blood cells, white blood cells, and platelets of a hematology analyzer in extended cell concentration ranges comprising the steps of:
   (a) providing a series of control compositions; each of said control compositions comprising a predetermined concentration of white blood cell analogs, stabilized red blood cells prepared by washing and suspension in a solution, in a concentration range from about $0.1\times10^6$ to about $9\times10^6$ cells per microliter, platelet analogs in a concentration up to $7,000\times10^3$ analogs per microliter, and a suspension medium; said concentration of said white blood cell analogs in said series of control compositions increasing in a range from $0.2\times10^3$ to $800\times10^3$ analogs per microliter and in at least one of said control compositions said white blood cell analogs being in an elevated concentration greater than $120\times10^3$ analogs per microliter, wherein when said white blood cell analogs in said control compositions are greater than $120\times10^3$ analogs per microliter, said concentration of said stabilized red blood cells is at least $1.5\times10^6$ cells per microliter to facilitate mono-dispersion of said elevated concentration of said white blood cell analogs; at least five of said control compositions having known assay values or known target ranges of white blood cell count, and at least five of said control compositions having known assay values or known target ranges of red blood cell count and hemoglobin concentration, and at least five of said control compositions having known assay values or known target ranges of platelet count;
   (b) mixing said control compositions by manual inversions or rotations, or rotating by a roller, of vials containing said control compositions to mono-disperse said elevated concentration of white blood cell analogs, said platelet analogs and said cells in said suspension medium;
   (c) analyzing each of said control compositions on a hematology analyzer, and obtaining report values of said white blood cell count, said red blood cell count, and said platelet count of each of said control compositions; and
   (d) determining linearity of enumerations of said white blood cells, said red blood cells, and platelets of said hematology analyzer, respectively, using said report values and known assay values or known target ranges of said white blood cell count, said red blood cell count, and said platelet count of said control compositions.

21. The method of claim 20, wherein said mixing of said control compositions to disperse said analogs and said cells in said suspension medium comprises a mixing time of less than 90 seconds.

22. The method of claim 21, wherein each of said control compositions is contained in one of said vials, and is used directly on said hematology analyzer after said mixing, without a manual dilution.

23. The method of claim 22, wherein said method uses at least two of said control compositions having said concentration of white blood cell analogs greater than $120\times10^3$ analogs per microliter.

24. The method of claim 23 further comprising in step (c) obtaining report values of hemoglobin concentration of said control compositions; and in step (d) determining linearity of hemoglobin measurement of said hematology analyzer using said report values of said hemoglobin concentration and known assay values or known target ranges of said hemoglobin concentration of said control compositions.

25. The method of claim 24, wherein said method further analyzes an aqueous solution not containing cellular particles to establish background of said enumerations.

26. The method of claim 25, wherein said method uses 14 or less said control compositions.

* * * * *